United States Patent
Koebel et al.

(10) Patent No.: US 8,366,978 B2
(45) Date of Patent: Feb. 5, 2013

(54) METHOD FOR DETERMINING SINTERING SHRINKAGE OF A PRE-SINTERED BODY

(75) Inventors: Stefan Koebel, Dachsen (CH); Wolfram Weber, Hilzingen (DE)

(73) Assignee: Metoxit AG, Thayngen (CH)

( * ) Notice: Subject to any disclaimer, the term of this patent is extended or adjusted under 35 U.S.C. 154(b) by 112 days.

(21) Appl. No.: 12/513,129

(22) PCT Filed: Nov. 5, 2007

(86) PCT No.: PCT/EP2007/009578
§ 371 (c)(1),
(2), (4) Date: Apr. 30, 2009

(87) PCT Pub. No.: WO2008/052807
PCT Pub. Date: May 8, 2008

(65) Prior Publication Data
US 2009/0273108 A1    Nov. 5, 2009

(30) Foreign Application Priority Data
Nov. 3, 2006 (DE) .......................... 10 2006 052 027

(51) Int. Cl.
*C04B 35/64* (2006.01)
*A61C 13/00* (2006.01)
(52) U.S. Cl. ........... 264/40.1; 264/18; 264/19; 264/662; 264/666; 264/672
(58) Field of Classification Search .................. 264/16, 264/17, 19, 40.1, DIG. 66, 603, 653, 662, 264/666, 672
See application file for complete search history.

(56) References Cited

U.S. PATENT DOCUMENTS

| | | | |
|---|---|---|---|
| 3,998,646 A | | 12/1976 | Weaver |
| 5,106,303 A | * | 4/1992 | Oden et al. ..................... 433/223 |
| 5,192,472 A | * | 3/1993 | Andersson ................... 264/40.1 |
| 5,565,152 A | * | 10/1996 | Od en et al. ...................... 264/19 |
| 6,106,747 A | * | 8/2000 | Wohlwend ....................... 264/16 |
| 6,354,836 B1 | | 3/2002 | Panzera et al. |
| 6,495,073 B2 | * | 12/2002 | Bodenmiller et al. .......... 264/16 |
| 6,570,320 B1 | | 5/2003 | Burkhardt et al. |

(Continued)

FOREIGN PATENT DOCUMENTS

| | | |
|---|---|---|
| DE | 19824783 | 12/1999 |
| EP | 0389461 | 9/1990 |

(Continued)

OTHER PUBLICATIONS

Rasmussen et al. "Optimum particle size distribution for reduced sintering shrinkage of a dental porcelain", Dental Matters, Jan. 13, 1997, pp. 43-50.*

(Continued)

*Primary Examiner* — Joseph Del Sole
*Assistant Examiner* — Nahida Sultana
(74) *Attorney, Agent, or Firm* — Leydig, Voit & Mayer, Ltd.

(57) ABSTRACT

A method for determining a sintering shrinkage of a pre-sintered body. The method includes providing a green pre-form with at least one design feature. The green-preform is pre-sintered to form a white body. At least one change in the at least one design feature with the pre-sintering is recorded. An expected sintering shrinkage to a dense-sintered component is determined using the recorded change.

15 Claims, 3 Drawing Sheets

U.S. PATENT DOCUMENTS

| | | | |
|---|---|---|---|
| 7,383,198 B1* | 6/2008 | Sepe | 705/8 |
| 8,178,012 B1* | 5/2012 | Khan et al. | 264/20 |
| 2005/0109060 A1* | 5/2005 | Cummings et al. | 65/17.6 |
| 2005/0110177 A1* | 5/2005 | Schulman et al. | 264/16 |
| 2005/0147944 A1* | 7/2005 | Karim et al. | 433/201.1 |
| 2008/0118894 A1* | 5/2008 | Rothbrust et al. | 433/215 |
| 2008/0303181 A1* | 12/2008 | Holand et al. | 264/16 |
| 2008/0312971 A2* | 12/2008 | Rosow et al. | 705/5 |
| 2010/0038807 A1* | 2/2010 | Brodkin et al. | 264/17 |
| 2010/0323327 A1* | 12/2010 | Eriksson et al. | 433/199.1 |
| 2011/0049738 A1* | 3/2011 | Sun et al. | 264/16 |
| 2011/0151411 A1* | 6/2011 | Schechner et al. | 433/222.1 |
| 2012/0214134 A1* | 8/2012 | Khan et al. | 433/201.1 |

FOREIGN PATENT DOCUMENTS

| | | |
|---|---|---|
| EP | 0858983 | 8/1998 |
| JP | 03124404 | 5/1991 |
| WO | WO-9947065 | 9/1999 |

OTHER PUBLICATIONS

International Search Report for International No. PCT/EP2007/009578, mailed on Jul. 15, 2008.

* cited by examiner

METHOD FOR DETERMINING SINTERING SHRINKAGE OF A PRE-SINTERED BODY

CROSS REFERENCE TO PRIOR APPLICATIONS

This application is a U.S. National Phase application under 35 U.S.C. §371 of International Application No. PCT/EP2007/009578, filed on Nov. 5, 2007 and which claims benefit to German Patent Application No. 10 2006 052 027.0, filed on Nov. 3, 2006. The International Application was published in German on May 8, 2008 as WO 2008/052807 A2 under PCT Article 21(2).

FIELD

The present invention relates to a method for determining the sintering shrinkage of a pre-sintered white body, the white body being formed by pre-sintering of a green preform.

BACKGROUND

It is known to pre-sinter green preforms to form a white body and to further process these later. The further processing can, for example, be a machining and/or a sintering. The degree of pre-sintering cannot be seen from external features of the white body. The degree of pre-sintering has a substantial influence on the shrinkage of the white body during sintering. It is therefore important to determine the degree of pre-sintering and to provide the white body with the information about the shrinkage when sintering to produce the fired component.

WO 99/47065 describes a method and a blank for the production of artificial tooth crowns and/or tooth bridges which fit onto at least one prepared stump.

However, the disadvantage here is that during production of the artificial denture, an enlargement ratio must be taken into account so as to compensate for the shrinkage, which is laboriously calculated from the apparent density of the white body and the achievable apparent density of the sintered body after sintering.

SUMMARY

An aspect of the present invention is to provide a method for determining an enlargement ratio which can quickly be carried out.

In an embodiment, the present invention provides for a method for determining a sintering shrinkage of a pre-sintered body. The method includes providing a green preform with at least one design feature. The green-preform is pre-sintered to form a white body. At least one change in the at least one design feature with the pre-sintering is recorded. An expected sintering shrinkage to a dense-sintered component is determined using the recorded change.

BRIEF DESCRIPTION OF THE DRAWINGS

The present invention is described in greater detail below on the basis of embodiments and of the drawings in which.

DETAILED DESCRIPTION

Figure 1:
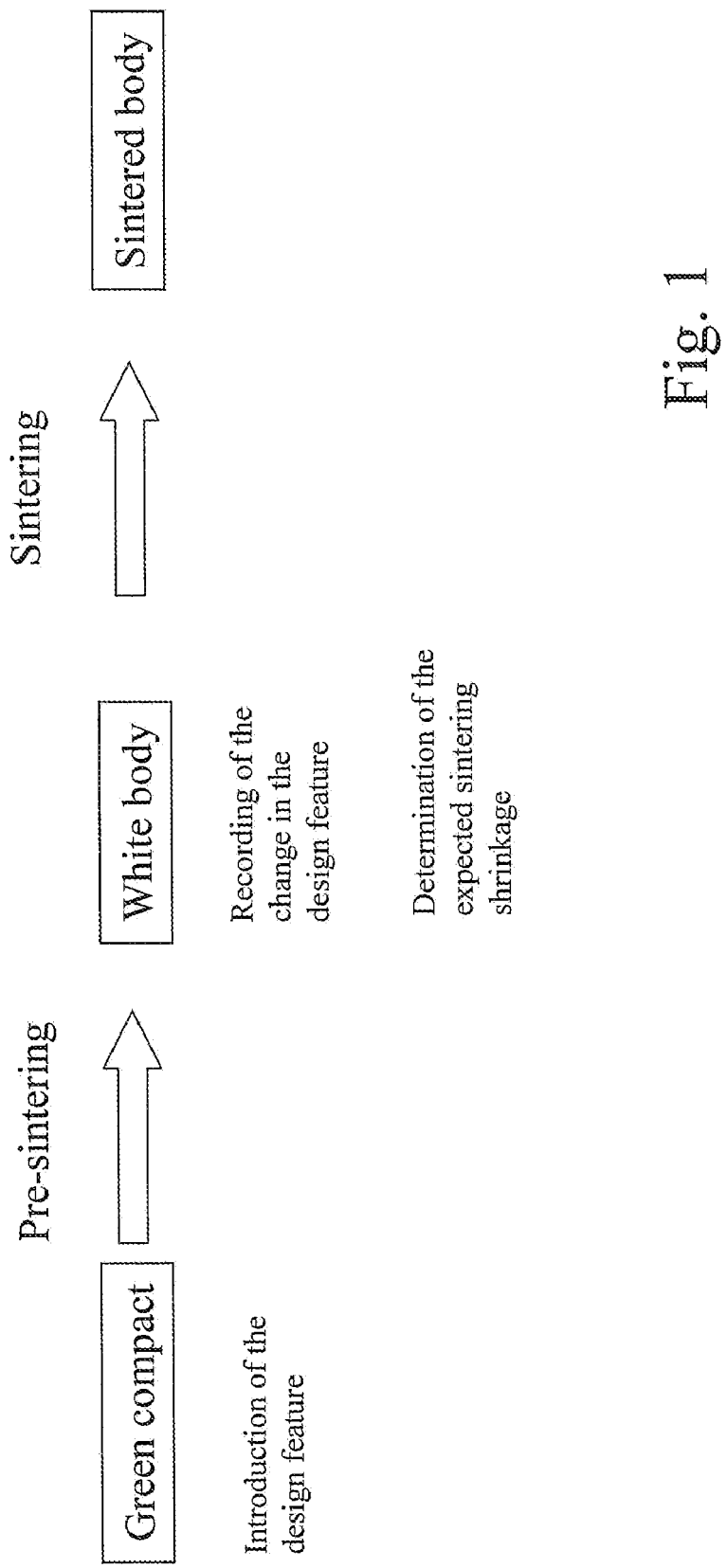
FIG. 1 shows a schematic representation of a method according to the present invention.

Any ceramic body which is pre-sintered in a later process to form a white body can be used as green preform. The white body can, for example, be sintered in a further subsequent process step to form a sintered body. The green perform can, for example, consists of metal or ceramic and particularly preferably of industrial-grade ceramic. The green preform can, for example, be produced by casting, plastic shaping and by compression moulding.

The design feature can, for example, characterize a dimension of the white body. It can, for example, be developed such that a measurement means can be attached thereto, for measuring. Grooves and holes are can be used as design features such as suitably designed surfaces and edges.

The green perform, or compact, is compacted during pre-sintering, but not yet as densely compacted as by the sintering. This can be achieved by a lower temperature than during sintering. After pre-sintering, the white body can, for example, be machined before full-sintering. A pre-compaction and pre-shrinkage of the green preform takes place during pre-sintering.

The design feature can be recorded manually, for example, with a calliper gauge or a micrometer. It can be recorded automatically, for example, in a measurement machine such as in a processing machine. During recording, the size of a design feature such as the distance between two design features, can be recorded.

Because the expected sintering shrinkage is determined, an enlargement ratio can be determined. The white body can be machined, using this enlargement ratio, such that the expected shrinkage is taken into account. The processing can thereby be adapted so as to minimize machining on the sintered body.

To determine the expected sintering shrinkage, the recorded dimensional change between the condition of the design feature, the green preform and its condition in the white body is related to the change exhibited by the design feature between its condition in the white body and its condition in the sintered body. The properties of the raw material, the production of the green preform and of the sintered body are set so that the expected shrinkage from white body to sintered body can be determined by measuring the design features.

The design feature can be recorded before the machining of the white body. The shrinkage during sintering can thereby be measured particularly precisely during sintering.

A first number of white bodies for which the expected sintering shrinkage to the dense-sintered component is determined can exceed a second number of green preforms on which changes in the design features during pre-sintering are recorded. The expected sintering shrinkage can thereby be determined particularly effectively. The second number of green preforms can be a random sample.

A length can be measured for each white body of the first number of white bodies. It is thereby possible to determine a feature that is simple to measure. A length is measured which can be determined by a design feature. It is thereby possible to predefine a length which is to be measured through the design feature.

The changes in the design features during sintering to the dense-sintered component can be recorded for the second number of green preforms. The changes in the design features are thereby recorded over the whole process. It is thereby possible to determine the expected sintering shrinkage of the first number of white bodies particularly precisely.

The density can be recorded for the second number of green preforms. It is thereby made possible to obtain information about the size of the possible shrinkage.

The density after sintering to the dense-sintered component can be recorded for the second number of green preforms. It is thereby made possible to obtain particularly precise information about the size of the possible shrinkage.

The green preform can be provided with the design feature by compression moulding. A high degree of precision is thereby achieved. In the case of a green preform which is formed by compression moulding, the design feature can be introduced directly during the pressing of the green preform. A separate production step is not necessary. The mould for the design feature can be integrated into the compression mould for pressing the green preform.

The green preform can be provided with the design feature by machining. This results in considerable freedom when choosing the shape and the orientation of the design features.

Turning, milling, grinding and drilling are used as machining processes. Because of the great freedom when configuring the design features when using these machining processes, these can be placed at particularly suitable places. The design features can, for example, be provided where there is a particularly large concentration of material. If different shrinkages are expected in specific directions, the design features can be arranged such that the dimensions to be recorded point in these directions.

The design feature can be recorded after pre-sintering in a processing machine. The delivery of the white bodies to a measurement machine or to a place at which design features are manually recorded can thereby be dispensed with. Moreover, the recorded values are thereby found directly on the machine where they are required. Furthermore, there is no need to allocate recorded values to the different pre-sintered white bodies, as the processing machine can immediately adapt and convert the processing program on the basis of the recorded values. It is also possible to manually record the design feature in the processing machine and manually adapt the machining process. A high degree of flexibility is thus achieved during determination of the shrinkage factor and during adaptation of the machining processes.

Any machine which can process white bodies can be used as a processing machine. CAD/CAM processing machines can, for example, be used. CAD/CAM milling and grinding processing machines can also be used. Complicated geometries can thereby be reliably produced. Moreover, the previously calculated shrinkage of the component during sintering of the white body can thus easily be taken into account during processing.

The distance between two design features can be recorded and the expected shrinkage during sintering determined with the recorded result. It is thereby possible to freely design the green preform in large areas without the need to introduce design features and still record values for a comparably long section.

Two holes at a distance from one another can be introduced into the green preform. These are designed as throughholes, for example, as blind holes. After pre-sintering, the distance between the two holes can be recorded. Two grooves can also be introduced into the green preform. To record the distance between the two grooves after pre-sintering, measuring instruments can be used which are designed to be less delicate than the measuring instruments for recording holes. The introduction of holes into the green preform represents a way of providing design features on the green preform. Moreover, a large part of the surface of the green preform is thus kept free of design features. A body which will display different shrinkage behaviour in different directions during pre-sintering and sintering can thereby be machined such that different degrees of shrinkage are thereby taken into account in different directions. The machining processes on the white body can thus be adapted particularly precisely to the shrinkage.

Different degrees of shrinkage in different directions can for example be due to the shape or the production of the body.

At least two design features can then introduced into the green preform, the green preform is pre-sintered, the design features are recorded after pre-sintering, and the shrinkage of the body is recorded from the recorded result. Thus the processing of the white body can be adapted to a different degree of shrinkage in different directions in space.

Several design features can be introduced into the green preform, these are recorded after the pre-sintering and an average for the expected shrinkage determined from the recorded values. A different degree of shrinkage in different areas of the body is thereby taken into account. Moreover, the processing data can be adapted to the different degrees of shrinkage. All processing measures for processing the white body can be determined using the same enlargement ratio.

For averaging, methods can be used which form an average of different numerical values. The arithmetic average, such as the weighted arithmetic average, is formed. When using the arithmetic average, the recorded values are added together and divided by the number of recorded values. In the case of the weighted arithmetic average, the individual recorded values are weighted according to frequency and importance.

The design feature can be an aperture. Thus the design feature can be introduced into the green preform by machining.

The green preform can consists of a ceramic material, such as zirconium oxide and/or aluminium oxide.

Partly stabilized zirconium oxide can be used. A particularly solid and tough sintered body is thereby produced. Polycrystalline, tetragonal zirconium oxide can, for example, also be used. An extremely fine texture can thereby be produced, as a result of which a very high mechanical strength of the sintered body is achieved.

The white body can be intended for further processing to form a component which can be used in the field of medicine, for example, in the field of dentistry.

High precision is required in the field of medicine, in particular in the field of dentistry. The shapes to be produced are often very complex. The use of components whose expected sintering shrinkage has been calculated in advance is therefore very widespread here. A large part or the whole processing can thereby already be undertaken on the white body and yet high precision can still be achieved. A simple method for determining the expected sintering shrinkage is particularly expedient here.

Test Carried Out:

A batch of a cuboidal green preform was prepared by compression moulding. The average green density was 3.000 g/cm$^3$, the maximum green density scatter was +/−0.015 g/cm$^3$, the standard deviation was less than 0.005 g/cm$^3$. The density of the individual green preforms was determined by weighing and measuring the edge lengths of the cuboidal green preforms.

This batch was then pre-sintered to form white bodies. The white bodies were machined and then dense-sintered. The density of the white bodies was 3.050 g/cm$^3$, the standard deviation of the density was 0.2 g/cm$^3$.

The batch was then full-sintered to form the dense-sintered components. The average density of the dense-sintered components was 6.060 g/cm$^3$. The densities of the bodies were between 6.050 g/cm$^3$ and 6.070 g/cm$^3$, the standard deviation was less than 0.003 g/cm$^3$.

The result was that the density scatter of the pre-sintered blanks was four times that of the green density and seven times that of the sintering density. Nearly identical densities in the green preforms and in the components that have been full-sintered can be assumed when determining the expected change in density.

Furthermore it was established that the scatters of the linear dimensions behave in exactly the same way as the densities. After pre-sintering, the dimensions scatter particularly strongly, but the weight scatter is less than 0.5%. The result is that the changes in density result substantially from changes in volume. By measuring a length, the same conclusions can therefore be drawn as by measuring a density.

FIG. 1 shows a schematic representation of a method according to the present invention. In a first production step, a green preform with defined density is produced by compression moulding from granular material. The green preform has a projection as a design feature. The position or the length or thickness of the projection is checked using a calliper gauge.

The green preform of known density is then pre-sintered to form a white body. The position or the length or the thickness of the projection changes in correlation to the degree of the sintering shrinkage during pre-sintering. The degree of pre-sintering of the white body is thus characterized by the design feature.

The white body is then clamped into a CAD-CAM processing machine. A sensor in the CAD-CAM processing machine records the position or the length or thickness of the projection. The geometry of the design features before the pre-sintering on the green preform of defined density and after the pre-sintering on the white body is used to determine the expected sintering shrinkage during sintering to form a sintered body of a defined density. This is based on the correlation of changes in geometry of the projection to the change in density of the body and the expected total shrinkage due to pre-sintering and sintering. An enlargement ratio for the processing of the white body is calculated on the basis of the expected sintering shrinkage. The green preform is then milled in the CAD-CAM processing machine using the CAD data with the help of the enlargement ratio to form an enlarged white body, e.g. a bridge skeleton.

After processing, the white body is fired to form a sintered body or a dense ceramic or the bridge skeleton. The bridge skeleton is then faced. The facing is applied like an enamel coat and fired on. The facing serves to imitate the colour of the individual teeth of the patient. Moreover, the properties of the facing correspond more closely to the natural enamel, with the result that an excessive detrition of the opposite natural tooth is avoided.

The homogeneity of the blanks used, plus precise knowledge of the sintering shrinkage of the blank, are decisive for the production of accurately fitting skeletons from porous zirconium oxide. The homogeneity of the blanks is guaranteed by the great care taken by the producer. The sintering shrinkage figure is obtained as a result of providing the green preforms with design features which change due to the pre-sintering.

Of the processes or process steps which have an influence on the precision of the overall process, which consists of the preparation of the granules, the compression moulding, the pre-sintering, the CAD/CAM processing and the sintering, it is the pre-sintering or the firing to form the porous blank where the greatest error occurs. The firing to form the porous blank determines, almost alone, the imprecision of the shrinkage. The other process steps can be carried out or monitored very precisely. The properties of the granules, the compression moulding and the optional green processing can be controlled very precisely. The density of the green preform before pre-sintering and the density of the sintered body after sintering can both be monitored very precisely. When firing the dental skeleton, the density can be relied upon to be always the same. The density fluctuates after pre-sintering. These fluctuations are caused by the raw material and/or the pre-sintering process. The total shrinkage from the green preform or moulding to the sintered body or to the dense ceramic is always the same here. The pre-sintering determines the loss or the shrinkage values from the white body to the sintered body or CAD-CAM block and from the machined white body or from the milling and/or grinding work to the sintered body or sintered skeleton. The degree of pre-sintering of the blank is decisive for the precision of the system. The degree of pre-sintering is characterized by the design features introduced into the green preform. Because a processing machine can ascertain the degree of pre-sintering by means of the design features, there is no need to also give the blank an enlargement ratio.

Figure 2:
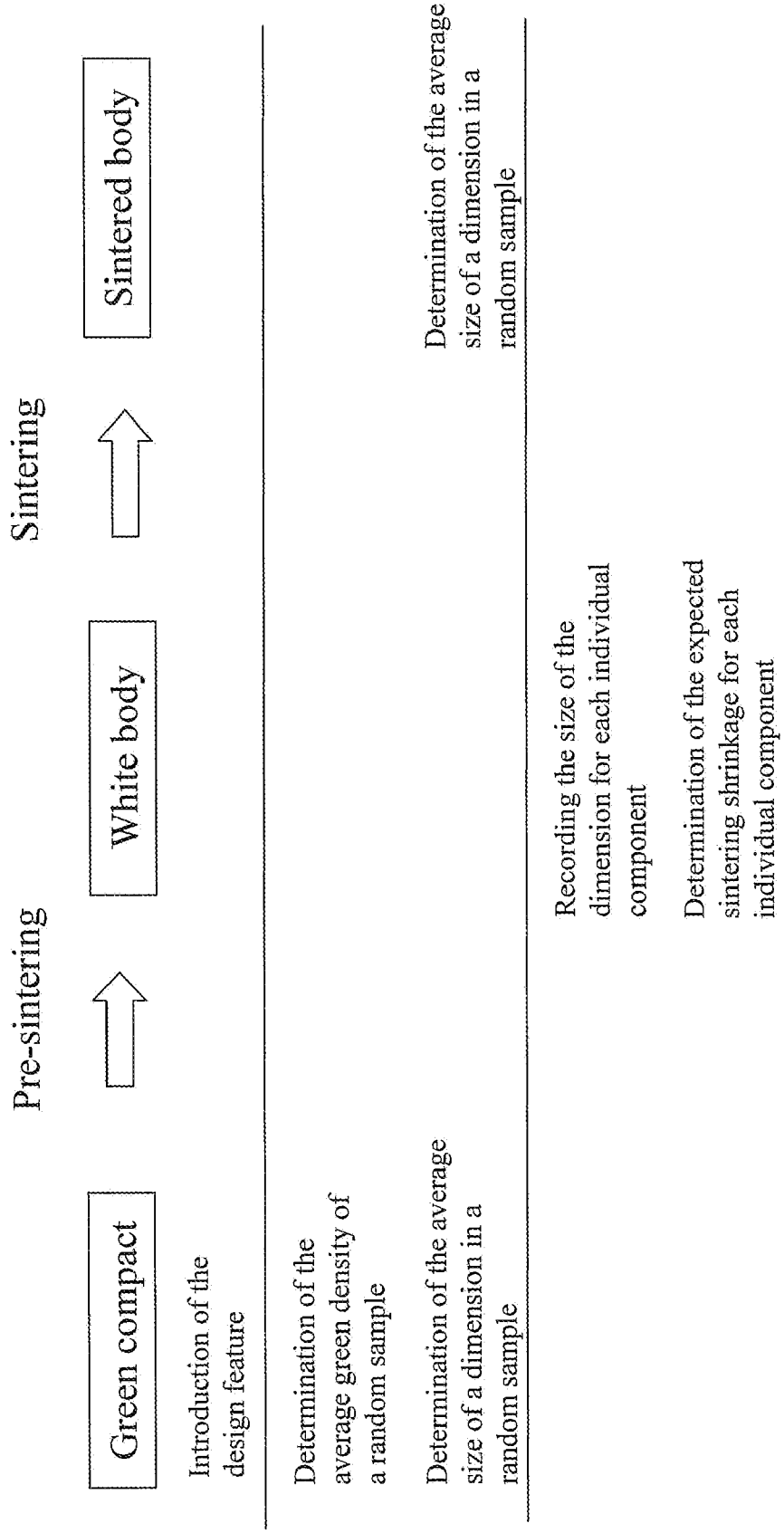
FIG. 2 shows a schematic representation of a further method according to the present invention.

FIG. 2 shows a schematic representation of a further method according to the present invention. Unlike the method shown in FIG. 1, the thickness of the projection is measured using a calliper gauge using a random sample of the green preforms and the average thickness determined. Moreover, in a random sample the density of individual green preforms is determined by measuring the volume and the weight. The average density of this random sample is then determined.

A random sample of the green preforms is full-sintered to form the white body and then the dense-sintered component or sintered body. The thickness of the projection is measured with this random sample and the average thickness determined. Moreover, the density of the individual components of the random sample is ascertained and the average density determined.

The green preforms are then pre-sintered to form white bodies. The thickness of the projection changes in correlation with the degree of the sintering shrinkage during pre-sintering. The degree of pre-sintering of the white body is thus characterized by the thickness of the projection.

The white body is then clamped into a CAD-CAM processing machine. A sensor in the CAD-CAM processing machine records the thickness of the projection. The expected sintering shrinkage during full sintering to the dense-sintered component is determined for each individual white body from the thickness of the projection at the respective white body, the average thickness of the projection in the random sample of the green compacts and the dense-sintered or full-sintered components, the average density of the green preforms and the average density of the dense-sintered components.

As in the method which is shown in FIG. 1, the enlargement ratio is determined on the basis of the expected sintering shrinkage and the white body further machined accordingly.

It is possible with this method, assuming that the dimension which is used to calculate the sintering shrinkage remains constant, to determine the sintering shrinkage even if the white body or the green preform has been machined. A processing can, for example, be the attachment of a holding means or the provision of features.

Moreover, it is possible with this method to achieve a relatively precise indication regarding the expected shrinkage with a small number of measurements. 3000 length measurements must be carried out for a batch of 3000 cuboidal blanks. There remain only the length and density measurements on the random sample. With a method according to the state of the art, 12000 measurements would have to be carried out for comparably precise information regarding the expected shrinkage. This would comprise 9000 measurements for the dimensions and 3000 measurements for the respective weight.

Figure 3:
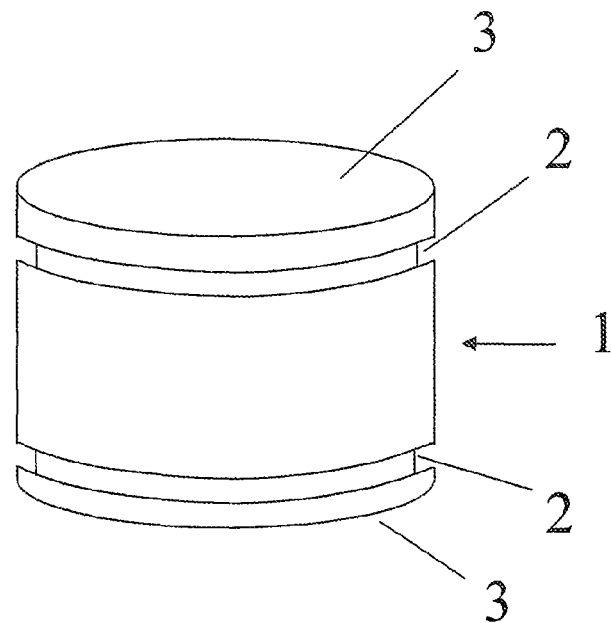
FIG. 3 shows a perspective view of a white body according to the present invention in a first embodiment.

FIG. 3 shows a perspective view of a white body 1 according to the present invention in an embodiment. The white body 1 is cylindrical. As design features, two circular grooves 2 have been turned into the white body. The two grooves 2 are arranged adjacent to the circular surfaces 3 of the cylinder.

This white body 1 is milled and/or ground into an enlarged crown skeleton in a CAD-CAM machine. The distance between the grooves 2 is measured in the CAD-CAM machine before the machining. The shrinkage during pre-sintering, and from this the expected shrinkage during sintering, is calculated from the measurement result and the distance between the two grooves 2 before pre-sintering. All the grooves 2 are made identical in all the white bodies 1 of this embodiment, with the result that the distance before the pre-sintering is always the same. The measured distance before the pre-sintering can therefore be input as a fixed value into the machine. The linear change in length, and from this the enlargement ratio for processing the white body, is calculated from the measured distances before and after pre-sintering.

Because the grooves 2 are set relatively far apart from one another, during measurement of the distance, the shrinkage of the white body 1 over a comparably large area can be taken into account and averaged. The expected shrinkage during sintering can thus be determined with great precision.

Because the grooves 2 are circumferential at many different points, the distance between the two grooves 2 can e.g. be measured by a CAD-CAM machine which also carries out the processing of the blank. The average can then be formed, from the individual measurement results with the result that measurement inaccuracies can be balanced out.

Figure 4:
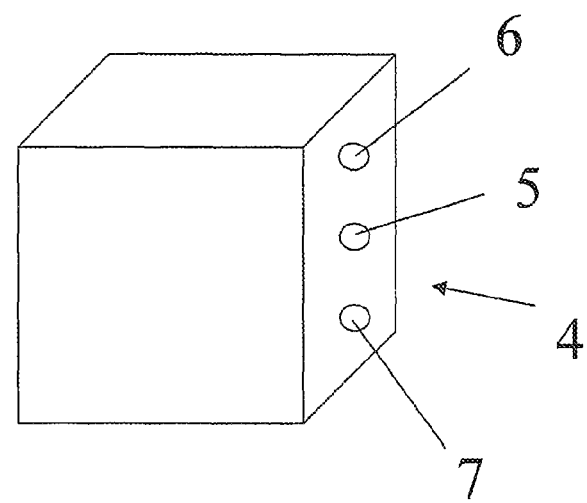
FIG. 4 shows a perspective view of a further embodiment of a white body according to the present invention.

FIG. 4 shows a perspective view of an embodiment of a white body 4 according to the present invention. The white body 4 according to the present invention is formed here as a cuboidal block 4. On one side of the block 4 three recesses 5, 6, 7 are introduced into the cuboid 4 as design features.

Before the white body 4 is machined, the expected sintering shrinkage is calculated. For this, the distance between the recesses 5, 6, 7 is measured in a separate machine by the user and processor of the white body and the expected sintering shrinkage is calculated by comparing this measured value with the distance, known to the machine, between the recesses 5, 6, 7 before the pre-sintering. The expected sintering shrinkage is then calculated from the degree of pre-sintering.

After the white body 4 has been sintered, there is an inlay which is particularly dimensionally stable.

The design features are used here additionally to identify the block. The total features tell the machine the size of the block and the material from which it is produced. Moreover, the design features represent reference points. These reference points are recognized by the machine's sensor. This is particularly helpful if the block needs to be reset while being machined.

The present application is not limited to embodiments described herein; reference should be had to the appended claims.

LIST OF REFERENCE NUMBERS

1 White Body
2 Groove
3 Circular surfaces
4 Cuboidal block
5 Middle recess
6 Outer recess
7 Outer recess

The invention claimed is:

1. Method for determining a sintering shrinkage of a pre-sintered body, the method comprising:
   providing a green preform having a predetermined full sintering shrinkage with at least one design feature;
   pre-sintering the green preform to form a white body resulting in at least one changed dimension of the at least one design feature;
   measuring the at least one changed dimension of the at least one design feature and recording the at least one changed dimension; and,
   calculating an expected sintering shrinkage from the pre-sintered white body to a dense-sintered component using the recorded at least one changed dimension.

2. The method as recited in claim 1, further comprising measuring a length of the white body.

3. The method as recited in claim 1, further comprising recording a density for the green preform.

4. The method as recited in claim 1, further comprising recording a density of the dense-sintered component.

5. The method as recited in claim 1, further comprising:
   recording a distance between two design features to obtain a first recorded result; and determining the expected sintering shrinkage using the first recorded result.

6. The method as recited in claim 1, wherein compression moulding is used to provide the at least one design feature to the green preform.

7. The method as recited in claim 1, wherein machining is used to provide the at least one design feature to the green preform.

8. The method as recited in claim 1, wherein the recording is performed using a processing machine after the pre-sintering.

9. The method as recited in claim 1, wherein;
   the at least one design feature includes at least two design features; and
   the determining includes calculating the shrinkage of the white body in various directions.

10. The method as recited in claim 1, wherein:
    the at least one design feature includes a plurality of design features;
    the recording includes recording the at least one change in the plurality of design features; and
    the determining includes determining an average of the expected shrinkage.

11. The method as recited in claim 1, wherein at least one design feature includes aperture.

12. The method as recited in claim 1, wherein the at least one design feature includes an indentation.

13. The method as recited in claim 1, wherein the white body includes a ceramic material.

14. The method as recited in claim 13, wherein the ceramic material includes at least one of zirconium oxide and aluminium oxide.

15. Method for determining a sintering shrinkage of a plurality of pre-sintered white bodies, the method comprising:
    measuring a dimension of a design feature of each of a sample of green preforms;
    sintering the sample of green preforms to form a corresponding sample of dense-sintered components so as to result in each dense-sintered component having a changed dimension of the respective design feature;
measuring the respective changed dimensions of the sample of dense-sintered components;
calculating an average changed dimension from the respective changed dimensions of the sample of dense-sintered components;
providing a plurality of green preforms, each green preform having a design feature and the plurality of green preforms exceeding the sample of green preforms and corresponding sample of dense-sintered components;
pre-sintering the plurality of green preforms to form a corresponding plurality of white bodies so as to result in each white body having a respective changed dimension of the respective design feature;
measuring the changed dimension of the design feature of each of the plurality of white bodies;
recording the changed dimension of each of the plurality of white bodies; and
calculating an expected sintering shrinkage for each of the plurality of white bodies based on the respective changed dimension of the respective design feature and the average changed dimension of the sample of dense-sintered components.

* * * * *